United States Patent
Kawagishi et al.

(10) Patent No.: US 9,519,866 B2
(45) Date of Patent: Dec. 13, 2016

(54) DIAGNOSIS SUPPORT APPARATUS, METHOD OF CONTROLLING THE SAME, AND STORAGE MEDIUM

(75) Inventors: Masami Kawagishi, Yokohama (JP); Yoshio Iizuka, Yokohama (JP); Kiyohide Satoh, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 44 days.

(21) Appl. No.: 13/305,565

(22) Filed: Nov. 28, 2011

(65) Prior Publication Data

US 2012/0136882 A1    May 31, 2012

(30) Foreign Application Priority Data

Nov. 30, 2010   (JP) ................................ 2010-267499

(51) Int. Cl.
- *G06F 17/30*     (2006.01)
- *G06N 7/00*      (2006.01)
- *G06F 19/00*     (2011.01)

(52) U.S. Cl.
CPC ......... *G06N 7/005* (2013.01); *G06F 17/30572* (2013.01); *G06F 19/345* (2013.01); *G06F 19/3443* (2013.01)

(58) Field of Classification Search
CPC ............ G06F 17/3053; G06F 17/30286; G06F 17/30528; G06F 17/30572; G06F 17/30554; G06F 17/30424
USPC ........... 707/754, E17.004, E17.019, E17.023
See application file for complete search history.

(56) References Cited

U.S. PATENT DOCUMENTS

| | | | |
|---|---|---|---|
| 6,292,577 B1 * | 9/2001 | Takahashi | 382/128 |
| 2002/0065460 A1 * | 5/2002 | Murao | 600/425 |
| 2010/0256991 A1 * | 10/2010 | Ishikawa et al. | 705/3 |
| 2011/0199390 A1 | 8/2011 | Iizuka et al. | 345/629 |
| 2011/0213748 A1 | 9/2011 | Kawagishi et al. | 706/52 |
| 2011/0262015 A1 | 10/2011 | Ishikawa et al. | 382/128 |

FOREIGN PATENT DOCUMENTS

| | | | | |
|---|---|---|---|---|
| JP | B 3226400 | | 11/2001 | |
| JP | 2002230518 A | * | 8/2002 | ........... G06F 19/321 |
| JP | A 2010-250690 | | 11/2010 | |

OTHER PUBLICATIONS

Doi, Kunio. "Computer-aided diagnosis in medical imaging: historical review, current status and future potential." Computerized medical imaging and graphics 31.4 (2007): 198-211.*

Chaum, Edward, et al. "Automated diagnosis of retinopathy by content-based image retrieval." Retina 28.10 (2008): 1463-1477.*

* cited by examiner

*Primary Examiner* — Nan Hutton
(74) *Attorney, Agent, or Firm* — Fitzpatrick, Cella, Harper & Scinto

(57) ABSTRACT

A diagnosis support apparatus which provides information for supporting medical diagnosis obtains known medical information of a diagnosis target held in a database as "already-input" information, and has a selection unit that selects non-input information to be presented as medical information, other than the already-input information. A similar-case obtaining unit obtains, using the already-input information and the presentation non-input information, a case including the presentation non-input information from a case database, as a case similar to that of the diagnosis target, and a presentation unit presents the presentation non-input information and the similar case.

13 Claims, 6 Drawing Sheets

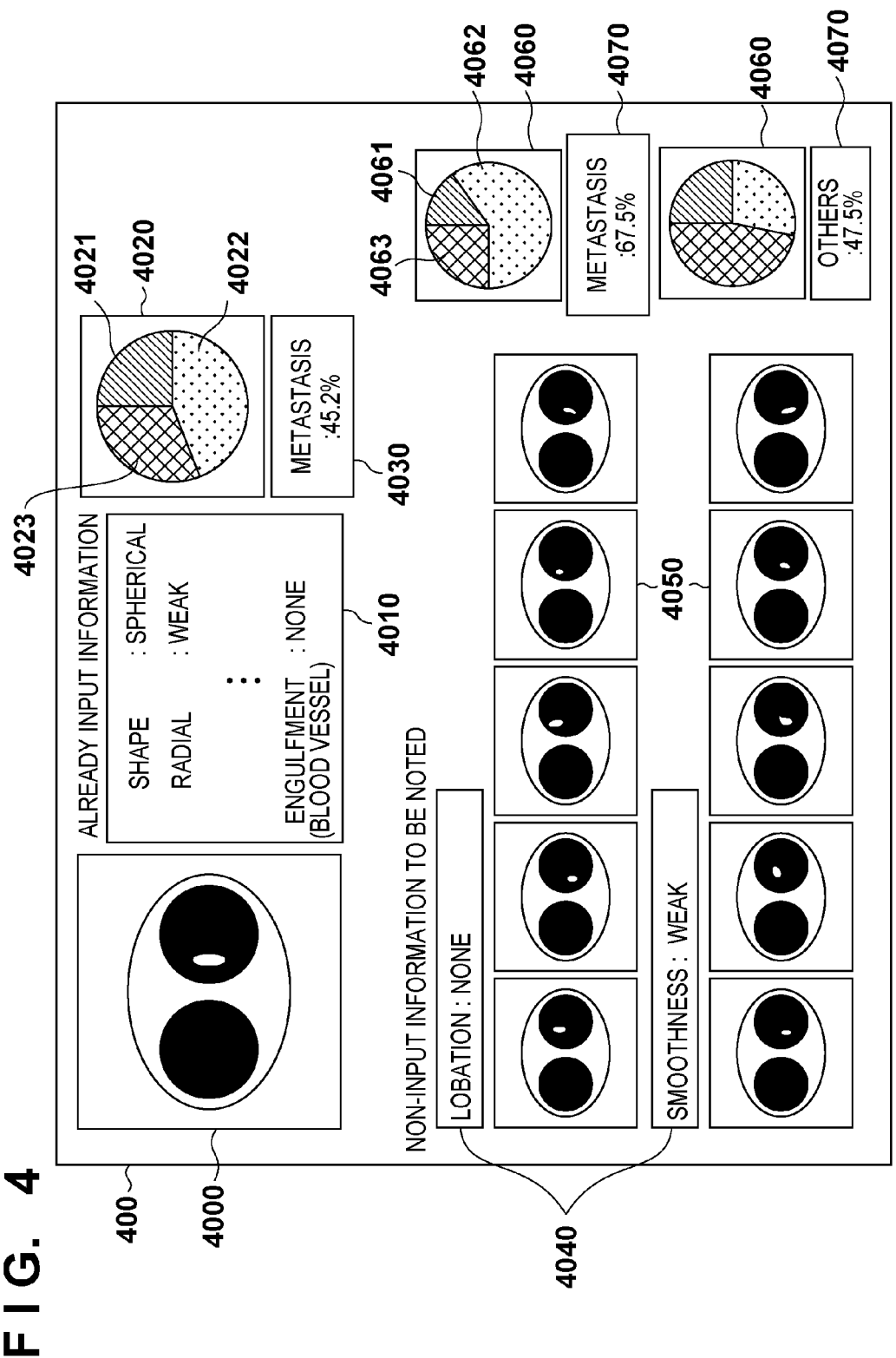

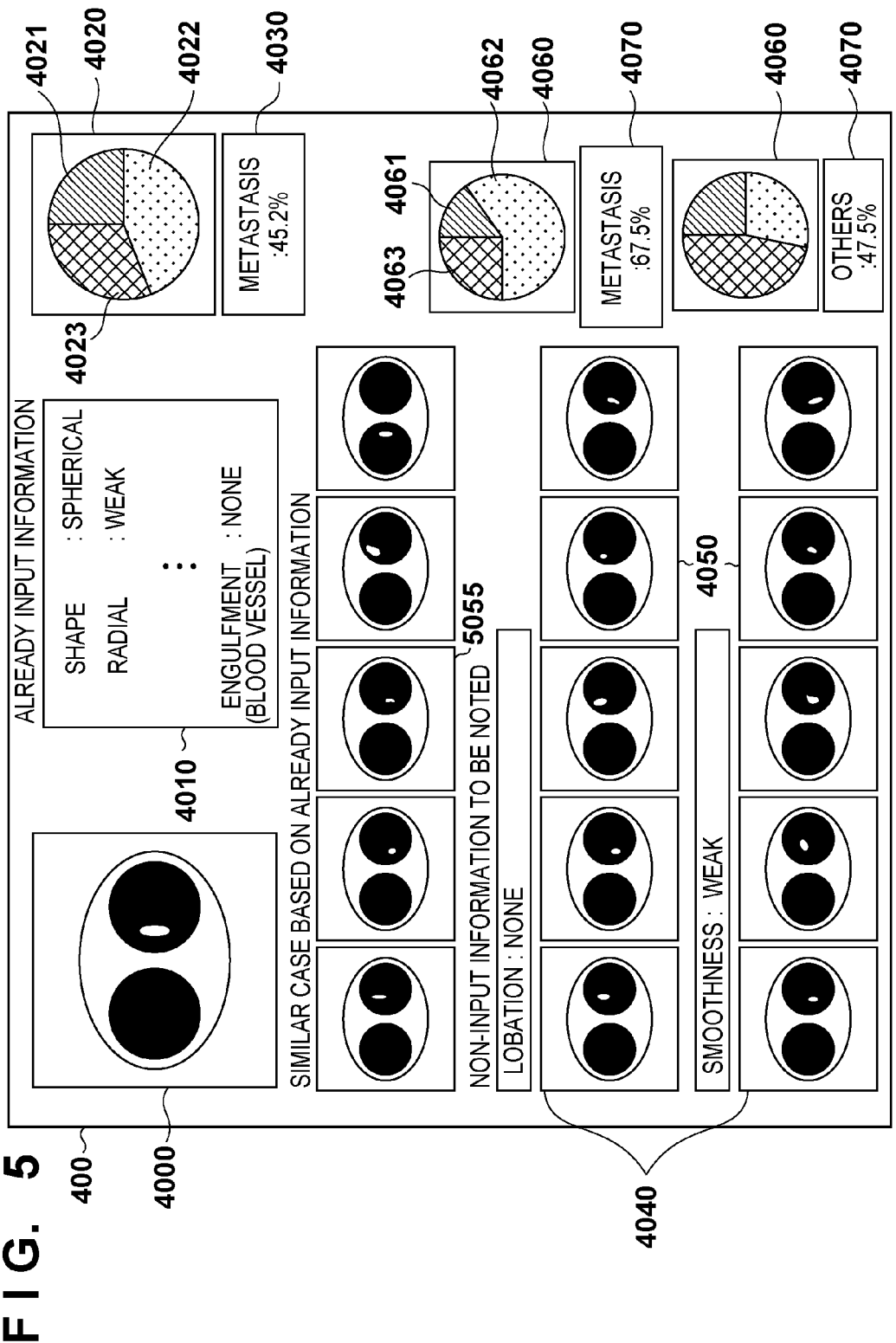

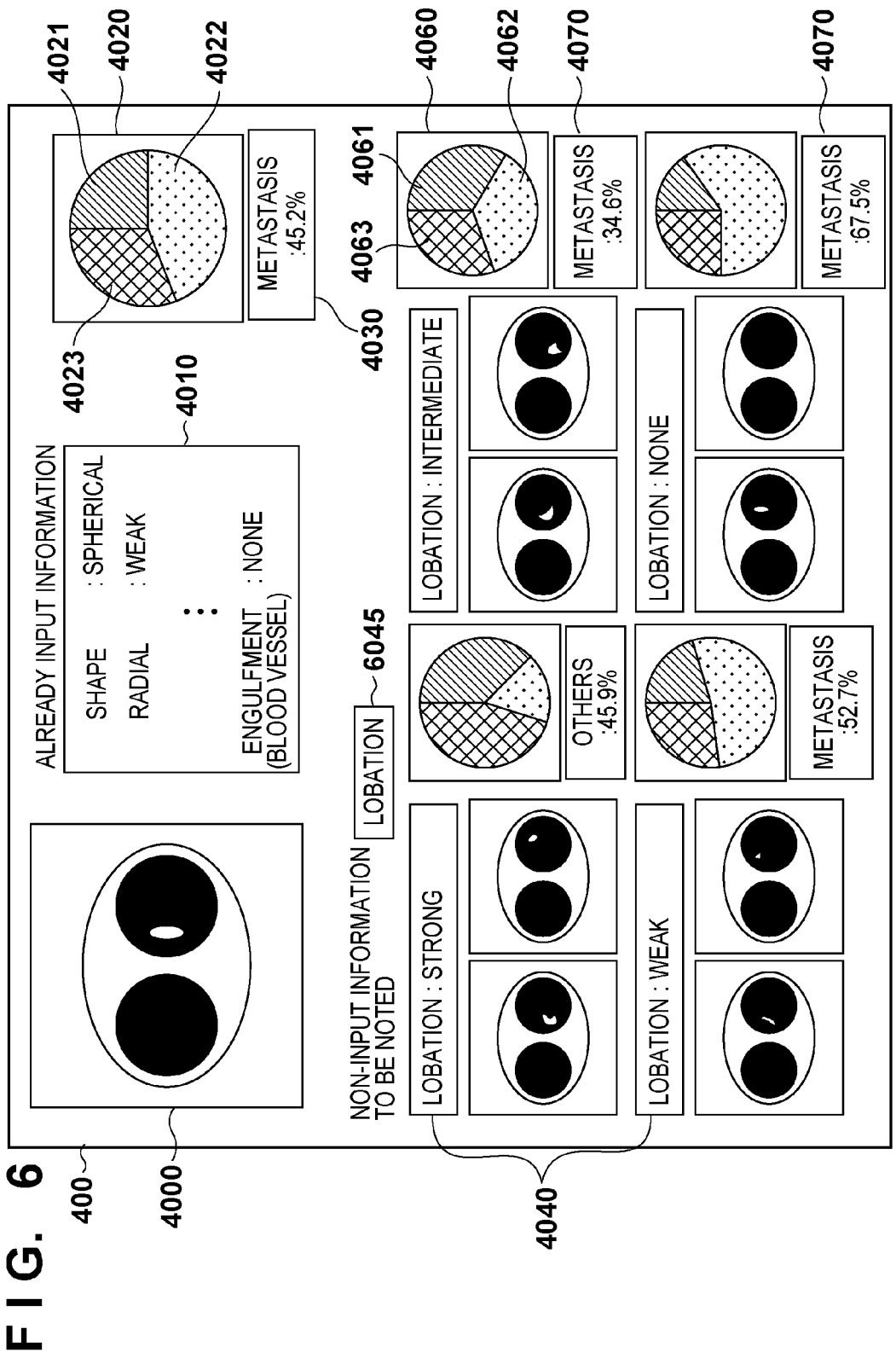

DIAGNOSIS SUPPORT APPARATUS, METHOD OF CONTROLLING THE SAME, AND STORAGE MEDIUM

BACKGROUND OF THE INVENTION

Field of the Invention

The present invention relates to a diagnosis support apparatus, a method of controlling the same, a storage medium and, more particularly, to a diagnosis support apparatus which provides information for supporting medical diagnosis, a method of controlling the same, and a storage medium.

Description of the Related Art

In the medical field, a doctor displays the medical images obtained by imaging a patient on a monitor, interprets the medical images displayed on the monitor, and observes the state of a morbid portion and temporal changes in it. Apparatuses which generate this type of medical images include, for example, an X-ray CT (Computed Tomography) apparatus, MRI (Magnetic Resonance Imaging) apparatus, and ultrasonic apparatus. Each diagnosis (imaging diagnosis) using these medical images can be divided into the step of finding an abnormal shade or the like from the medical images as diagnosis targets and obtaining the characteristics of the shade and the step of performing differential diagnosis to identify the shade.

Conventionally, there has been developed a medical diagnosis support apparatus which infers the identification of an abnormal shade by using the characteristics (interpretation findings) of the shade as input information and presents the resultant information for the purpose of supporting differential diagnosis by doctors. For example, there has been proposed an apparatus which calculates the probability of a given shade in a chest X-ray CT image being a malignant tumor and the probability of the shade being a benign tumor and presents the resultant information. In general, the following is a proper procedure when using such an apparatus in an actual clinical site. First of all, the doctor performs differential diagnosis. The doctor then refers to the inference result output from the medical diagnosis support apparatus as reference information.

A problem in this case is that if there are many pieces of information which have not been input (to be referred to as "non-input information" hereinafter), the accuracy of inference by the medical diagnosis support apparatus is low. Attempts have therefore been made to obtain more reliable inference results by making an apparatus select non-input information necessary for inference and prompt the doctor to add the information. Prompting the doctor to check non-input information greatly influencing an inference result allows one to expect an improvement of the certainty factor of diagnosis by the doctor himself/herself. In addition, there can be expected a reduction of diagnosis errors caused by interpretation oversights.

For example, Japanese Patent No. 3226400 has disclosed a technique of selecting and presenting non-input information to be noted from the inference result (current inference result) obtained by an apparatus based on information which has already been input (to be referred to as "already input information" hereinafter) and the inference result obtained when non-input information is added to already input information. This technique is designed to calculate the degree of influence of each piece of non-input information with respect to a current inference result and to present non-input information exhibiting a high influence degree. This makes it possible to present non-input information which greatly influences the inference result obtained by the apparatus based on already input information.

When the apparatus disclosed in Japanese Patent No. 3226400 presents non-input information to be noted, the doctor as a user determines by himself/herself whether the information exists in a medical image, by interpreting the original image. At this time, there is no clue presented, other than the original image, by which the doctor determines whether the information exists, and hence it sometimes takes much time for the doctor to perform the determination, or he/she sometimes cannot properly perform the determination.

In consideration of the above problem, the present invention provides a technique of allowing a doctor to efficiently determine the presence/absence of non-input information to be noted.

SUMMARY OF THE INVENTION

According to one aspect of the present invention, there is provided a diagnosis support apparatus which provides information for supporting medical diagnosis, the apparatus comprising: a medical information obtaining unit adapted to obtain known information of medical information of a diagnosis target held in a database as already input information; a selection unit adapted to select, as presentation non-input information, non-input information to be presented from non-input information as medical information other than the already input information; a similar case obtaining unit adapted to obtain, using the already input information and the presentation non-input information, a case including the presentation non-input information from a case database as a similar case similar to a case of the diagnosis target; and a presentation unit adapted to present the presentation non-input information and the similar case.

According to one aspect of the present invention, there is provided a method of controlling a diagnosis support apparatus which provides information for supporting medical diagnosis, the method comprising: obtaining known information of medical information of a diagnosis target held in a database as already input information; selecting, as presentation non-input information, non-input information to be presented from non-input information as medical information other than the already input information; obtaining, using the already input information and the presentation non-input information, a case including the presentation non-input information from a case database as a similar case similar to a case of the diagnosis target; and presenting the presentation non-input information and the similar case.

Further features of the present invention will be apparent from the following description of exemplary embodiments with reference to the attached drawings.

BRIEF DESCRIPTION OF THE DRAWINGS

FIG. 4 is a view showing an example of presented information according to the first embodiment;

FIG. 5 is a view showing an example of presented information according to the second embodiment; and FIG. 6 is a view showing an example of presented information according to the third embodiment.

DESCRIPTION OF THE EMBODIMENTS

Exemplary embodiments of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

A medical diagnosis support apparatus according to the first embodiment obtains known medical information associated with a given case as a diagnosis target as already input information, and performs diagnosis support associated with the case.

The following description is based on an example of using the medical diagnosis support apparatus to obtain interpretation findings associated with an abnormal shade in a lung as input information, perform inference about the type of abnormality (diagnosis name) of the abnormal shade, and present diagnosis support information based on the inference result. Obviously, the target of such an inference process is not limited to this example, and the diagnosis names, the items of interpretation findings which can be input, and the like each are merely an example to explain the steps in the processing performed by the medical diagnosis support apparatus.

Figure 1:
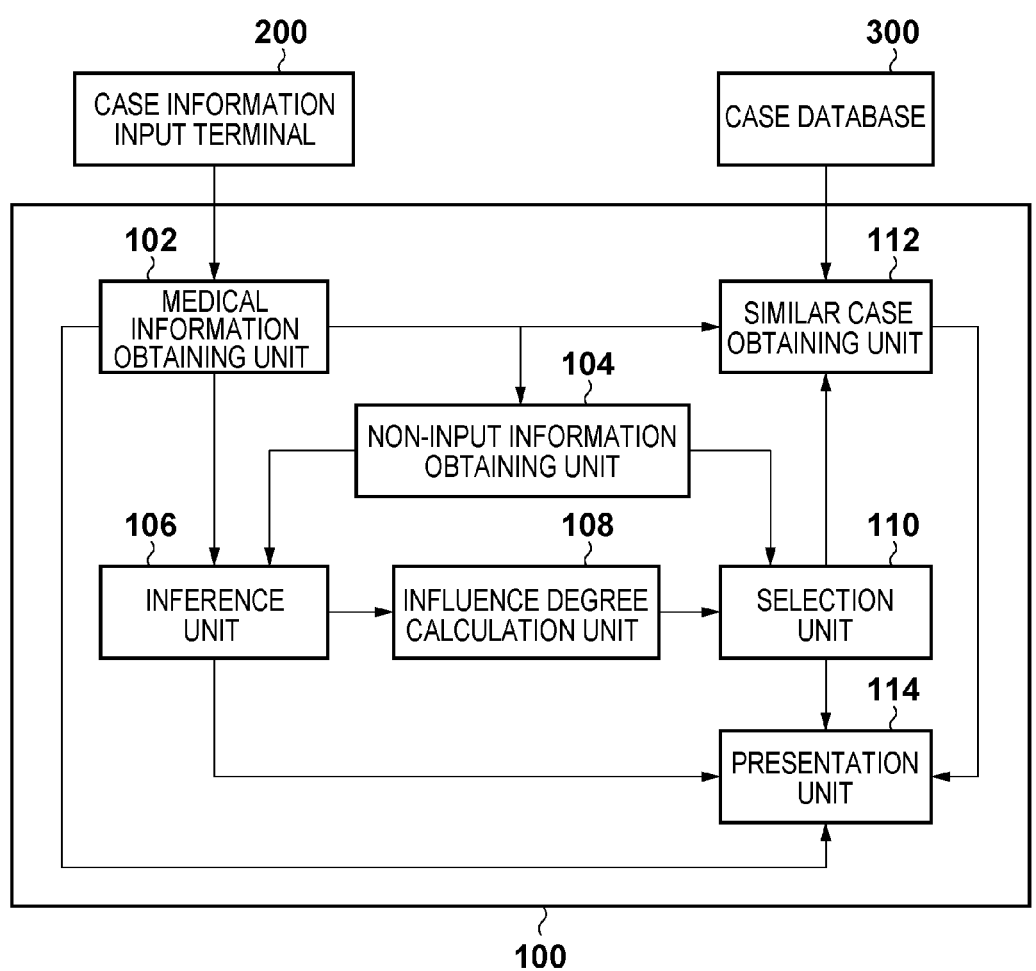
FIG. 1 is a block diagram showing the equipment configuration of a diagnosis support apparatus according to the first embodiment.

FIG. 1 shows the arrangement of a medical diagnosis support apparatus according to the first embodiment. A medical diagnosis support apparatus 100 according to this embodiment is connected to a case information input terminal 200 and a case database 300.

The case information input terminal 200 obtains information about an abnormal shade in the lung (for example, the information of medical images and electronic medical records) with respect to a case as a diagnosis target from a server (not shown). Alternatively, external storage devices such as an FDD, HDD, CD drive, DVD drive, MO drive, and ZIP drive may be connected to the apparatus to obtain data from them. The apparatus then displays, on the monitor, these pieces of information in a form that allows a user (doctor) to interpret them, and obtains the interpretation findings input by the user which it then handles as already input information. In this embodiment, the user inputs interpretation findings relating to the medical image displayed on the monitor by using a mouse and a keyboard. Note that this processing is implemented by making the case information input terminal 200 have a function of allowing the user to select information with a GUI by using, for example, interpretation finding input support method based on a template form. The case information input terminal 200 transmits already input information about the abnormal shade in the lung and accompanying data (representative images and the like) to a medical diagnosis support apparatus 100 via a LAN or the like in accordance with a request from the user.

The case database 300 stores already input information such as interpretation findings about abnormal shades in the lungs and accompanying data in association with many cases acquired in the past. The case database 300 has a general similar case retrieval function of outputting, upon receiving a combination of input information, as a similar case, a case having already input information identical or similar to the input information. Using this function allows the user to obtain similar cases, the total number of similar cases, and the like. Obviously, information which can be obtained is not limited to these pieces of information. Information about items which can be input, which the case database 300 has, is input to the medical diagnosis support apparatus 100 via a LAN or the like.

The medical diagnosis support apparatus 100 includes a medical information obtaining unit 102, a non-input information obtaining unit 104, an inference unit 106, an influence degree calculation unit 108, a selection unit 110, a similar case obtaining unit 112, and a presentation unit 114.

The medical information obtaining unit 102 obtains already input information about an abnormal shade in the lung, which has been input from the case information input terminal 200 to the medical diagnosis support apparatus 100, and accompanying data, and outputs them to the non-input information obtaining unit 104, the inference unit 106, the similar case obtaining unit 112, and the presentation unit 114.

The non-input information obtaining unit 104 obtains, as non-input information, at least one set of information based on information obtained by subtracting already input information from all the pieces of information which can be input (that is, information other than already input information). The obtained non-input information is output to the inference unit 106 and the selection unit 110.

The inference unit 106 executes inference based on the already input information with respect to the abnormal shade in the lung as a diagnosis target which is obtained by the medical information obtaining unit 102, and calculates the probability (already input information inference result) of the abnormal shade being each diagnosis name recorded on the case database. The inference unit 106 calculates the probability (non-input information inference result) of the abnormal shade being each diagnosis name assuming that non-input information of a pair of already input information and each non-input information obtained by the non-input information obtaining unit 104 is additionally added. The obtained already input information inference result and each non-input information inference result are output to the influence degree calculation unit 108 and the presentation unit 114.

The influence degree calculation unit 108 calculates the influence degree of each piece of non-input information with respect to inference by using the already input information inference result obtained by the inference unit 106 and each non-input information inference result. The obtained influence degree is output to the selection unit 110.

The selection unit 110 selects non-input information to be presented from non-input information based on the influence degree of each piece of non-input information obtained by the influence degree calculation unit 108. The selection unit 110 then outputs the selected presentation non-input information to the presentation unit 114.

The similar case obtaining unit 112 obtains a similar case from the case database 300 based on a combination of the already input information obtained by the medical information obtaining unit 102 and the presentation non-input information obtained by the selection unit 110. The similar case obtaining unit 112 then outputs the obtained similar case to the presentation unit 114.

The presentation unit 114 generates information to be presented based on the already input information obtained by the medical information obtaining unit 102, the inference result obtained by the inference unit 106, the presentation non-input information obtained by the selection unit 110, and the similar case obtained by the similar case obtaining unit 112.

Note that at least some of the respective processing units of the medical diagnosis support apparatus 100 shown in FIG. 1 may be implemented as independent devices. In addition, each unit may be implemented as software for implementing each function. Assume that in this embodiment, each processing unit is implemented by software.

Figure 2:
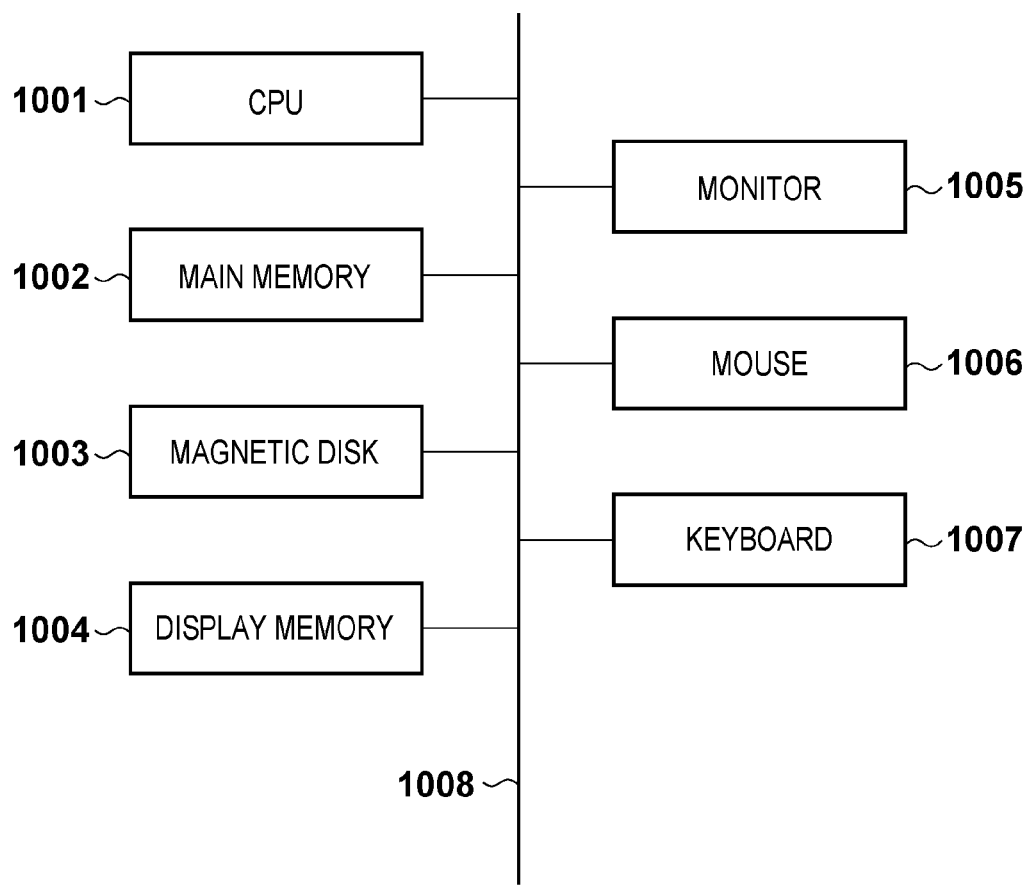
FIG. 2 is a block diagram showing the basic arrangement of a computer which implements each processing unit of the diagnosis support apparatus by software.

FIG. 2 shows the basic arrangement of a computer for implementing the function of each processing unit shown in FIG. 1 by executing software. A CPU 1001 controls the operation of each constituent element. A main memory 1002 stores control programs executed by the CPU 1001, and provides a work area at the time of execution of a program by the CPU 1001. A magnetic disk 1003 stores an operating system (OS), device drives for peripheral devices, and various types of application software including programs for the execution of processing (to be described later). A display memory 1004 temporarily stores the display data generated by the presentation unit 114. A monitor 1005 is, for example, a CRT monitor or liquid crystal monitor, and displays images, texts, and the like based on data from the display memory 1004. A mouse 1006 and a keyboard 1007 are respectively used by the user to perform input operations such as pointing input operation and inputting of characters and the like. The respective constituent elements are communicatively connected to each other via a common bus 1008.

Figure 3:
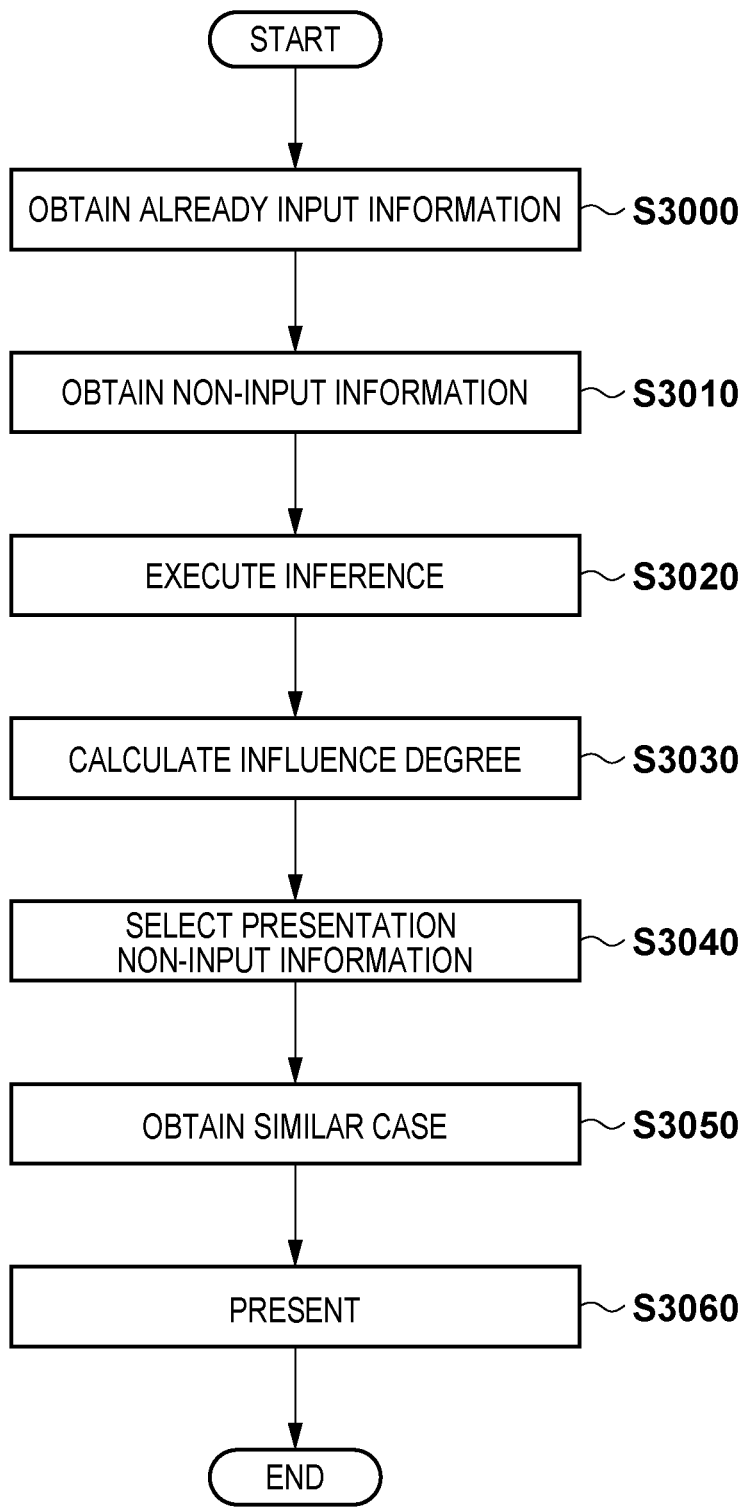
FIG. 3 is a flowchart showing an overall processing procedure according to the first embodiment.

A processing procedure in the medical diagnosis support apparatus 100 will be described next with reference to the flowchart of FIG. 3. This embodiment is implemented by causing the CPU 1001 to execute a program which is stored in the main memory 1002 and implements the function of each processing unit.

Assume that in the following description, this apparatus handles, as input information, interpretation findings constituted by n types of interpretation finding items and the states of the respective items. Each interpretation finding item name is represented by $1j$ ($j=1$ to n), and a state name (discrete value) which $1j$ can take is written as $Sjk$. The range of k takes various values depending on $1j$. This embodiment allows inputting, for example, of interpretation finding items (finding names) shown in Table 1. In addition, the respective interpretation finding items (finding names) can take corresponding states (state names), as shown in the table.

TABLE 1

| j | lj (Item Name) | jk | Sjk (State Name) |
|---|---|---|---|
| 1 | Shape | 11 | Spherical |
|   |       | 12 | Lobulated |
|   |       | 13 | Irregular |
| 2 | Lobation | 21 | Strong |
|   |          | 22 | Intermediate |
|   |          | 23 | Weak |
|   |          | 24 | None |
| 3 | Radial | 31 | Strong |
|   |        | 32 | Intermediate |
|   |        | 33 | Weak |
|   |        | 34 | None |
| . . . |
| n | Engulfment | n1 | Present |
|   | (Blood Vessel) | n2 | Suspicious |
|   |   | n3 | Absent |

For example, "Shape" of 11 represents the shape of an abnormal shade, and takes three states, namely S11 "spherical", S12 "lobulated", and S13 "irregular". "Lobation" of 12 represents the degree of lobation in an abnormal shade, and takes four states, namely S21 "strong", S22 "intermediate", S23 "weak", and S24 "none". "Radial" of 13 represents the degree of radial state of an abnormal shade, and takes four states, namely S31 "strong", S32 "intermediate", S33 "weak", and S34 "none". In addition, "Engulfment (Blood Vessel)" of 1n represents the presence/absence of the engulfment of a blood vessel in an abnormal shade, and takes three states, namely Sn1 "present", Sn2 "suspicious" indicating the suspicion of engulfment, and Sn3 "none".

In the following description, a set of $1j$ is written as N, and a set of $Sjk$ is written as E. Assume however that a plurality of states $Sjk$ corresponding to a given interpretation finding item $1j$ do not simultaneously exist in one E. For example, if 11 takes S11, S12, and S13, and 12 takes S21, S22, S23, and S24, E={S11, S21} holds, but E={S11, S12} does not hold. This is because one interpretation finding item takes only one state.

In this case, a set of interpretation finding items corresponding to already input information is written as Nf, and a set of states of Nf is written as Ef. A set of interpretation finding items corresponding to information other than already input information is written as ¬Nf, and a set of states in ¬Nf which can be combined as elements is written as Evm (m=1, 2, . . . ). In this case, the sign "¬" represents negation. Ef and Evm respectively correspond to already input information and non-input information. In addition, the influence degree of the non-input information Evm is written as IR(Evm).

In the following description, a diagnosis name is written by using the symbol "D". In this embodiment, diagnosis names take three values, namely primary lung cancer, lung cancer metastasis, and others, respectively written as D1, D2, and D3. In addition, the inference probability of a diagnosis name Dr (r=1, 2, 3) when E is given as input information is written as P(Dr|E).

In step S3000, the medical information obtaining unit 102 obtains already input information about an abnormal shade in the lung input to the medical diagnosis support apparatus 100 and accompanying data. Assume that the interpretation finding information which the medical diagnosis support apparatus 100 has obtained in step S3000 is 11 "Shape": S11 "spherical", 13 "Radial": S33 "weak", . . . , 1n "Engulfment (Blood Vessel)": Sn3 "none". In this case, the set Nf of interpretation finding items of the already input information is given as Nf={11, 13, . . . , 1n}, and the set Ef of the states of Nf is given as Ef={S11, S33, . . . , Sn3}.

In step S3010, the non-input information obtaining unit 104 obtains, as non-input information, at least one set based on information obtained by excluding the already input information from all the information which can be input. Consider, for example, a case in which ¬Nf={12, 16, 18}, 12 takes S21, S22, S23, and S24, 16 takes S61 and S62, and 18 takes S81, S82, and S83. If, for example, the number of elements to be included in Evm is limited to one, the non-input information obtaining unit 104 obtains 4+2+3=9 pieces of non-input information. Alternatively, if the number of elements to be included is limited to 1 or 2, the non-input information obtaining unit 104 obtains 9+4×2+4×3+2×3=35 pieces of non-input information.

In step S3020, the inference unit 106 infers the probability (already input information inference result) P(D$_r$|E$_f$) of the abnormal shade being each diagnosis name based on the already input information (that is, Ef) of the abnormal shade in the lung obtained in step S3000. In addition, the inference unit 106 infers the probability (non-input information inference result) $P(D_r|E_f \cup E_{vm})$ of the abnormal shade being each diagnosis name by pairing the already input information and each piece of the non-input information (that is, Evm) obtained in step S3010.

As an inference means at this time, it is possible to use one of various existing inference techniques such as a Bayesian network, neural network, and support vector machine. This embodiment uses a Bayesian network as an inference means. The Bayesian network is an inference model using conditional probabilities. It is possible to obtain the inference probability of each diagnosis name when already input information is input (the probability of the case being each diagnosis name; also called a posterior probability). In this embodiment, the inference unit 106 obtains the probabilities of types D1, D2, and D3 of abnormal shades.

In step S3030, the influence degree calculation unit 108 calculates the influence degree of each piece of non-input information by using the inference result obtained in step S3020. The influence degree calculation unit 108 calculates the absolute value of the difference between the probability as the already input information inference result and the probability as the non-input information inference result as the influence degree of the non-input information. More specifically, the influence degree calculation unit 108 calculates an influence degree IR(Evm) of the non-input information Evm by the following equation. Note however that Dmax is Dr which maximizes $P(Dr|Ef)$.

$$IR(E_{vm}) = |P(D_{max}|E_f) - P(D_{max}|E_f \cup E_{vm})| \qquad (1)$$

That is, considering a diagnosis name (that is, Dmax) inferred as exhibiting the highest probability when based on the already input information, the degree of variation in inference probability upon addition of non-input information is considered as the inference degree of the non-input information.

In step S3040, the selection unit 110 selects presentation non-input information based on the influence degree IR(Evm) of each piece of non-input information obtained in step S3030. Assume that in this embodiment, a predetermined number of pieces of non-input information selected in descending order of influence degree are given as presentation non-input information.

In step S3050, the similar case obtaining unit 112 obtains a similar case from the case database 300 based on the already input information obtained in step S3000 and the presentation non-input information obtained in step S3040. Note that if there are a plurality of pieces of presentation non-input information, similar processing is performed for each piece of information.

It is possible to obtain a similar case from the case database 300 by a general method of generating a query to select a case simultaneously including already input information and presentation non-input information and executing the query with respect to the case database 300. Alternatively, the similar case obtaining unit 112 may obtain retrieval results by a general similarity retrieval method of obtaining the degree of coincidence between the already input information and the input information of each case and obtaining ranked results based on the degrees of coincidence, and then obtain a case including presentation non-input information as a similar case among the retrieval results. The latter method can obtain, as a similar case, even a case which does not completely include the already input information.

In step S3060, the presentation unit 114 displays, on the monitor 1005, the information (already input information and a representative image) about the abnormal shade in the lung obtained in step S3000 and the already input information inference result obtained in step S3020. In addition, the presentation unit 114 displays, on the monitor 1005, the presentation non-input information selected in step S3040, the representative image added to the similar case obtained in step S3050, and the non-input information inference result based on the presentation non-input information obtained in step S3020.

FIG. 4 shows an example of presented information displayed on the monitor 1005 in this embodiment. Presented information 400 includes a representative image 4000 of the abnormal shade in the lung, already input information 4010 of the abnormal shade in the lung obtained in step S3000, and an already input information inference result 4020 inferred in step S3020. In the example shown in FIG. 4, the monitor 1005 displays in a pie chart, as the already input information inference result 4020, an inference probability 4021 of a primary lung cancer in the already input information inference result, an inference probability 4022 of a lung cancer metastasis, and inference probability 4023 of others. In addition, the presented information 400 includes a diagnosis name ("lung cancer metastasis" in the example shown in FIG. 4) exhibiting the highest inference probability among the respective diagnosis names in the already input information inference result and a probability 4030 of the diagnosis name (the inference probability of the lung cancer metastasis in the example shown in FIG. 4). The presented information 400 also includes two pieces of presentation non-input information 4040 selected in step S3040 and representative images 4050 of similar cases (associated with the respective pieces of presentation non-input information) obtained in step S3050. In addition, the presented information 400 includes a non-input information inference result 4060 based on the presentation non-input information inferred in step S3020. In the example shown in FIG. 4, the monitor 1005 displays, as the non-input information inference result 4060 in a pie chart, an inference probability 4061 of a primary lung cancer in the non-input information inference result, an inference probability 4062 of the lung cancer metastasis, and an inference probability 4063 of others. The presented information 400 also includes a diagnosis name exhibiting the highest inference probability among the respective diagnosis manes in the non-input information inference result and a probability 4070 of the diagnosis name. In the example shown in FIG. 4, the probabilities 4070 are metastasis: 67.5%, and other: 47.5%.

According to this embodiment, the doctor can determine whether non-input information exists in a medical image as a diagnosis target, while referring to medical images by using images of past cases, as clues, which include both already input information and presentation non-input information. This allows the doctor to efficiently and accurately perform this determination.

Second Embodiment

The first embodiment is configured to obtain and present similar cases by using already input information and presentation non-input information. However, it is possible to present other kinds of similar cases. A medical diagnosis support apparatus according to the second embodiment obtains and presents a second similar case by using only already input information.

Note that the medical diagnosis support apparatus according to this embodiment has the same arrangement as that shown in FIG. 1 in the first embodiment. However, the second embodiment differs from the first embodiment in that a similar case obtaining unit 112 obtains a similar case by using already input information and presentation non-input information and also obtains a second similar case by using only already input information. The second embodiment further differs from the first embodiment in that a presentation unit 114 generates and displays information to be presented based on the second similar case obtained by the similar case obtaining unit 112 in addition to already input information, an inference result, retrieval non-input information, and a similar case. The basic arrangement of a computer which implements a medical diagnosis support apparatus 100 by executing software is the same as that shown in FIG. 2 in the first embodiment. A flowchart for explaining the overall processing performed by the medical diagnosis support apparatus 100 is the same as that shown in FIG. 3. However, the processing in steps S3050 and S3060 partly differs from that in the first embodiment. Only the differences between the overall processing performed by the medical diagnosis support apparatus 100 according to this embodiment and that performed in the first embodiment will be described below with reference to the flowchart of FIG. 3.

The processing in each of steps S3000 to S3040 is the same as that in the first embodiment.

In step S3050, the similar case obtaining unit 112 obtains a similar case (first similar case) using already input information and presentation non-input information by performing the same processing as that in step S3050 in the first embodiment. The similar case obtaining unit 112 obtains a second similar case from a case database 300 based on the already input information obtained in step S3000. The similar case obtaining unit 112 then outputs the first and second similar cases to the presentation unit 114.

Note that it is possible to obtain the second similar case by the same method as that used in the first embodiment. More specifically, it is possible to obtain the second similar case from the case database 300 by a general method of generating a query to select a case including input information coinciding (or exhibiting a high degree of coincidence) with already input information and executing the corresponding operation for the case database 300.

In step S3060, the presentation unit 114 performs the same processing as that in step S3060 in the first embodiment. That is, the presentation unit 114 displays, on a monitor 1005, a non-input information inference result based on information (already input information and a representative image) about an abnormal shade in the lung, an already input information inference result, presentation non-input information, a representative image added to the first similar case, and the presentation non-input information. The presentation unit 114 further displays the representative image added to the second similar case obtained in step S3050 on the monitor 1005.

FIG. 5 shows an example of presented information displayed on the monitor 1005 in this embodiment. The example shown in FIG. 5 includes a representative image 5055 of the second similar case in addition to the example in FIG. 4.

This embodiment simultaneously presents an image of a past case including both already input information and presentation non-input information and an image of a past case including already input information (not necessarily including presentation non-input information). This allows the doctor to compare them. That is, adding presentation non-input information allows the doctor to determine whether the non-input information exists in a medical image of a diagnosis target, by referring to whether a similar image is obtained by the medical image of the diagnosis target. This makes it possible for the doctor to perform the determination efficiently and accurately.

Third Embodiment

In the first embodiment, non-input information which greatly influences inference is selected as presentation non-input information. However, a method of selecting presentation non-input information is not limited to this, and other methods can be used. A medical diagnosis support apparatus according to the third embodiment selects presentation non-input information by performing processing different from that in the first embodiment.

Note that the arrangement of the medical diagnosis support apparatus according to this embodiment is the same as that shown in FIG. 1 in the first embodiment. Note however that the processing performed by a selection unit 110 differs from that in the first embodiment. Only the differences between the medical diagnosis support apparatus according to this embodiment and that according to the first embodiment will be described below.

The basic arrangement of a computer which implements a medical diagnosis support apparatus 100 by executing software is the same as that shown in FIG. 2 in the first embodiment. A flowchart for explaining the overall processing performed by the medical diagnosis support apparatus 100 is the same as that shown in FIG. 3. However, the processing in step S3040 partly differs from that in the first embodiment. Only the differences between the overall processing performed by the medical diagnosis support apparatus 100 according to this embodiment and that performed in the first embodiment will be described below with reference to the flowchart of FIG. 3.

The processing in each of steps S3000 to S3030 is the same as that in the first embodiment.

In step S3040, the selection unit 110 decides one piece (Evt) of presentation non-input information based on an influence degree IR(Evm) of each non-input information obtained in step S3030. For example, the selection unit 110 selects non-input information exhibiting the highest influence degree with respect to inference. The selection unit 110 then obtains a set (Nvt) of interpretation finding items included in the selected presentation non-input information. The selection unit 110 then selects all the combinations (obviously including Evt) which the state of Nvt can take. That is, the selection unit 110 selects a plurality of interpretation findings with different states in the same item as presentation non-input information. Note that a selection method to be used is not limited to this, and it is possible to select some of all the combinations which the state of Nvt can take as presentation non-input information.

If, for example, interpretation finding {S24 (Lobation—none)} is decided as Evt, Nvt is {12 (Lobation)}. If 12 takes states S21, S22, S23, and S24, four pieces of information {S21}, {S22}, {S23}, and {S24} are selected as presentation non-input information.

The processing in each of steps S3050 and S3060 is the same as that in the first embodiment.

FIG. 6 shows an example of presented information displayed on the monitor 1005 in this embodiment. The example shown in FIG. 6 includes, as presentation non-input information, interpretation findings (Nvt) 6045 representing all states ({strong, intermediate, weak, none}) associated with a given item ("Lobation" in the example shown in FIG. 6).

According to this embodiment, the doctor can compare a diagnosis target image with each of images of past cases each including each of a plurality of pieces of non-input information with different states in the same item and already input information. This allows the doctor easily to determine which one of the states associated with the item should be added as an interpretation finding.

Fourth Embodiment

In each embodiment described above, in step S3000, the doctor interprets the medical image displayed by the medical diagnosis support apparatus 100, and obtains interpretation findings as input information. However, the types of input information and the method of obtaining input information are not limited to these examples. For example, it is possible to use, as input information (already input information/non-input information), medical examination data including past interpretation reports and medical records associated with an object to be examined, other kinds of information which can be used for diagnosis support processing, and the like.

Fifth Embodiment

According to each embodiment described above, in step S3030, the influence degree calculation unit 108 obtains the influence degree of non-input information with respect to a diagnosis name exhibiting the highest inference probability upon inputting of already input information. However, it is possible to obtain the influence degree of non-input information for each diagnosis name. In step S3040, a selection unit 110 selects presentation non-input information exhibiting a high influence degree for each diagnosis name. In step S3050, a similar case obtaining unit 112 may obtain a similar case for each diagnosis name. In step S3060, a presentation unit 114 may present information about the presentation non-input information selected for each diagnosis name and a representative image of a similar case. This allows the user to determine whether non-input information influencing a diagnosis name other than a diagnosis name obtained as an already input information inference result exists in an image.

In step S3030, the influence degree calculation unit 108 may obtain an influence degree as a value that can be positive or negative without using any absolute value in equation (1). In step S3040, the selection unit 110 then selects non-input information exhibiting the highest influence degree in a positive value and non-input information exhibiting the highest influence degree in a negative value (absolute value). In step S3050, the similar case obtaining unit 112 obtains a similar case for each piece of presentation non-input information in each of positive and negative values. In step S3060, the presentation unit 114 may present information about each piece of presentation non-input information and a representative image of a similar case. This allows the user to determine whether non-input information giving a positive influence on already input information inference result and non-input information giving a negative influence to the result exist in an image. It is also possible to select presentation non-input information by another method other than a method using an influence degree with respect to inference. For example, it is possible to define priorities with respect to the respective interpretation findings in advance and select non-input information exhibiting a high priority.

According to the present invention, the doctor can efficiently determine the presence/absence of non-input information to be noted.

Other Embodiments

Aspects of the present invention can also be realized by a computer of a system or apparatus (or devices such as a CPU or MPU) that reads out and executes a program recorded on a memory device to perform the functions of the above-described embodiments, and by a method, the steps of which are performed by a computer of a system or apparatus by, for example, reading out and executing a program recorded on a memory device to perform the functions of the above-described embodiments. For this purpose, the program is provided to the computer for example via a network or from a recording medium of various types serving as the memory device (for example, computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-267499 filed on Nov. 30, 2010, which is hereby incorporated by reference herein in its entirety.

What is claimed is:

1. A diagnosis support apparatus which provides medical information to a medical image, the apparatus comprising:
   at least one processor and memory, the memory including a list of items of information inputtable or computable for the medical image, coupled to each other and cooperating to act as:
   a medical information obtaining unit adapted to obtain from said memory first information selected from a set of information which has been input by a user and/or computed by a computer for the medical image;
   a first selection unit adapted to select at least one piece of second information for the medical image, said at least one piece of second information being other than the first information and being selected from the set of information;
   an inference unit adapted to infer a first diagnosis of the medical image based on the first information, and infer a second diagnosis of the medical image based on the first information and the selected at least one piece of second information;
   a second selection unit adapted to select the at least one piece of second information to be presented based on an influence degree which indicates influence of the at least one piece of second information on inference of the first diagnosis;
   a similar-case obtaining unit adapted to obtain from images stored in a case database a similar image, based on a similarity between (1) information, associated with the medical image, including the first information and the second information selected by the second selection unit, and (2) information associated with the image stored in the case database; and
   a presentation control unit adapted to present a subset of the at least one piece of obtained second information and the obtained similar image,
   wherein the second information for the medical image is a second item selected from the items which are not input by a user and/or are not computed by a computer.

2. The apparatus according to claim 1, wherein said similar-case obtaining unit further obtains a second similar case similar to a case of the diagnosis target from the case database based on the first information, and said presentation control unit presents the similar case and the second similar case.

3. The apparatus according to claim 1, wherein said selection unit selects the at least one piece of second information by which a diagnosis name different from the diagnosis name is obtained as an inference result, in a case where said inference unit performs inference based on the first information and information which is different from the first information.

4. The apparatus according to claim 1, wherein said influence degree is a difference between a probability obtained by using the first information and a probability obtained by using the at least one piece of second information.

5. The apparatus according to claim 4, wherein said selection unit selects the at least one piece of second information to be presented by a predetermined number of pieces of information in descending order of the influence degree.

6. The apparatus according to claim 1, wherein said selection unit selects, as the at least one piece of second information, at least one item selected from the group consisting of a shape of the diagnosis target, a degree of lobation of the diagnosis target, a radial degree of the diagnosis target, and the presence/absence of engulfment of a blood vessel, and selects at least one piece of information indicating a state of the item selected from the group consisting of information indicating a type of the shape, information indicating a degree of the lobation, information indicating the radial degree, and information indicating the presence/absence of engulfment of the blood vessel.

7. The apparatus according to claim 6, wherein said selection unit selects, as the at least one piece of second information, the item corresponding to the second information which is included in the one piece of information and exhibits the highest influence degree, and the one piece of information formed from a plurality of pieces of the second information including the second information corresponding to the item.

8. A method of controlling a diagnosis support apparatus which provides medical information to a medical image, the method comprising:
obtaining from a memory first information selected from a set of information which has been input by a user and/or computed by a computer for the medical image;
selecting at least one piece of second information for the medical image, said at least one piece of second information being other than the first information and being selected from the set of information;
inferring a first diagnosis of the medical image based on the first information, and inferring a second diagnosis of the medical image based on the first information and the selected at least one piece of second information;
selecting the at least one piece of second information to be presented based on an influence degree which indicates influence of the at least one piece of second information on inference of the first diagnosis;
obtaining a similar image from images stored in a case database based on a similarity between (1) information associated with the medical image including the first information and the second information selected in the second selecting and (2) information associated with the image stored in the case database; and
presenting a subset of the at least one piece of obtained second information and the obtained similar image,
wherein the second information for the medical image is a second item selected from the items which are not input by a user and/or are not computed by a computer.

9. A non-transitory computer-readable storage medium storing a computer program for causing a computer to execute each step in a method of controlling a diagnosis support apparatus which provides medical information to a medical image, the method comprising:
obtaining from a memory first information selected from a set of information which has been input by a user and/or computed by a computer for the medical image;
selecting at least one piece of second information for the medical image, said at least one piece of second information being other than the first information and being selected from the set of information;
inferring a first diagnosis of the medical image based on the first information, and inferring a second diagnosis of the medical image based on the first information and the selected at least one piece of second information;
selecting the at least one piece of second information to be presented based on an influence degree which indicates influence of the at least one piece of second information on inference of the first diagnosis;
obtaining a similar image from images stored in a case database based on a similarity between (1) information, associated with the medical image, including the first information and the second information selected in the second selecting and (2) information associated with the image stored in the case database; and
presenting a subset of the at least one piece of obtained second information and the obtained similar image,
wherein the second information for the medical image is a second item selected from the items which are not input by a user and/or are not computed by a computer.

10. A diagnosis support apparatus which provides medical information to a medical image, the apparatus comprising:
at least one processor and memory, the memory including a list of items of information inputtable or computable for the medical image, coupled to each other and cooperating to act as:
an already input information obtaining unit adapted to obtain from said memory already input information selected from a set of information which has been input by a user and/or computed by a computer for a medical image of a diagnosis target;
a non-input information obtaining unit adapted to obtain non-input information for diagnosis target, said non-input information being other than the already input information and being selected from the set of information;
a first selection unit adapted to select presentation non-input information from the obtained non-input information to be presented as reference information for the diagnosis target;
an inference unit adapted to infer a first diagnosis of the medical image based on the input information, and infer a second diagnosis of the medical image based on the input information and the selected non-input information;
a second selection unit adapted to select the at least one piece of non-input information to be presented based on an influence degree which indicates influence of the at least one piece of non-input information on inference of the first diagnosis;
a similar case obtaining unit adapted to obtain a case including the already input information and the presentation non-input information selected by the second selection unit from a case database as a similar case to the diagnosis target; and a presentation unit adapted to present the presentation non-input information and the obtained similar case, wherein the non-input information for the medical image is a second item selected from the items which are not input by a user and/or are not computed by a computer.

11. The apparatus according to claim 10, further comprising:

an influence degree calculation unit adapted to calculate an influence degree for one of the obtained non-input information, using an inference result from an interference unit using the obtained already input information and the one of the obtained non-input information, wherein the selection unit is configured to select non-input information to be presented from the obtained non-input information based on the influence degree of each of the obtained non-derived information obtained by the influence degree calculation unit.

12. A diagnosis support apparatus which provides medical information to a medical image, the apparatus comprising:

at least one processor and memory coupled to each other and cooperating to act as:

a medical information obtaining unit adapted to obtain from said memory first information selected from a set of information which has been input by a user and/or computed by a computer for the medical image;

a selection unit adapted to select at least one piece of second information for the medical image, said at least one piece of second information being other than the first information and being selected from the set of information;

a similar-case obtaining unit adapted to obtain a similar image from images stored in a case database based on a similarity between (1) information associated with the medical image including the first information and the second information, and (2) information associated with the image stored in the case database; and a presentation control unit adapted to present a subset of the at least one piece of obtained second information and the obtained similar image, wherein the apparatus further comprises an influence degree calculation unit configured to calculate a difference between a probability obtained by using the first information and a probability obtained by using the at least one piece of second information as an influence degree indicating influence of the at least one piece of second information on inference of the diagnosis name, and wherein said selection unit selecting the at least one piece of second information to be presented based on the influence degree.

13. A method of controlling a diagnosis support apparatus comprising at least one coupled processor and memory which provides medical information to a medical image, the method comprising:

obtaining from said memory first information selected from a set of information which has been input by a user and/or computed by a computer for the medical image;

selecting at least one piece of second information for the medical image, said at least one piece of second information being other than the first information and being selected from the set of information;

obtaining a similar image from images stored in a case database based on a similarity between (1) information associated with the medical image including the first information and the second information, and (2) information associated with the image stored in the case database;

presenting a subset of the at least one piece of obtained second information and the obtained similar image, wherein the apparatus calculates a difference between a probability obtained by using the first information and a probability obtained by using the at least one piece of second information as an influence degree indicating influence of the at least one piece of second information on inference of the diagnosis name, and wherein said selection unit selects the at least one piece of second information to be presented based on the influence degree.

* * * * *